United States Patent
Yager et al.

(10) Patent No.: US 9,778,261 B2
(45) Date of Patent: Oct. 3, 2017

(54) POROUS MEMBRANE-BINDING PEPTIDES

(71) Applicant: University of Washington, Seattle, WA (US)

(72) Inventors: Paul Yager, Seattle, WA (US); Caitlin Anderson, Seattle, WA (US); David Baker, Seattle, WA (US); Yu-Ru Lin, Seattle, WA (US); Carly Holstein, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/272,650

(22) Filed: Sep. 22, 2016

(65) Prior Publication Data

US 2017/0082624 A1   Mar. 23, 2017

Related U.S. Application Data

(60) Provisional application No. 62/222,118, filed on Sep. 22, 2015.

(51) Int. Cl.

| | | |
|---|---|---|
| *A61K 39/395* | (2006.01) | |
| *A61K 39/00* | (2006.01) | |
| *C07K 16/28* | (2006.01) | |
| *C07H 21/04* | (2006.01) | |
| *C12N 15/10* | (2006.01) | |
| *G01N 33/569* | (2006.01) | |
| *C07K 14/00* | (2006.01) | |

(52) U.S. Cl.
CPC ....... *G01N 33/56983* (2013.01); *C07K 14/00* (2013.01); *C07K 14/001* (2013.01); *C07K 2319/43* (2013.01); *C07K 2319/70* (2013.01); *G01N 2333/11* (2013.01)

(58) Field of Classification Search
CPC ........ A61K 2039/505; C07K 2317/565; C07K 2317/21; C07K 2317/92; C07K 2317/24
See application file for complete search history.

(56) References Cited

FOREIGN PATENT DOCUMENTS

| WO | WO2008070179 | * | 6/2008 |
|---|---|---|---|
| WO | 2012/018907 A2 | | 2/2012 |
| WO | 2013/138259 A2 | | 9/2013 |
| WO | 2014/152946 A2 | | 9/2014 |
| WO | 2015/143339 A2 | | 9/2015 |
| WO | 2016/033168 A1 | | 3/2016 |

OTHER PUBLICATIONS

Baker (Jul. 2011) "Protein engineering: navigating between chance and reason," Nature Methods, 8(8):623-626.
Byrnes et al. (Nov. 2013) "Progress in the development of paper-based diagnostics for low-resource point-of-care setting," Bioanalysis, 5(22):2821-2836.
Chin et al. (Jun. 2012) "Commercialization of microfluidic point-of-care diagnostic devices," Lab on a Chip, 12(12):2118-2134.
Fridley et al. (Apr. 2013) "The evolution nitrocellulose as a material for bioassays," MRS Bulletin, 38(4):326-330.
Karanicolas et al. (Apr. 2011) "A de novo protein binding pair by computational design and directed evolution," Molecular Cell, 42(2):250-260.
Liu et al. "Solution nmr structure of de novo designed fr55, northeast structural genomics consortium (Nesg) target pr109," available online at: https://www.ncbi.nlm.nih.gov/Structure/pdb/2MTL (Aug. 2014).
Tinberg et al. (Sep. 2013) "Computational design of ligand-binding proteins with high affinity and selectivity," Nature, 501(7466):212-216.

* cited by examiner

*Primary Examiner* — Janet L Andres
*Assistant Examiner* — Barry A Chestnut
(74) *Attorney, Agent, or Firm* — McDonnell Boehnen Hulbert & Berghoff LLP (57) ABSTRACT

The present invention provides porous membrane-binding polypeptides, fusion proteins thereof, and methods for use of the polypeptides and fusion proteins in binding assays.

19 Claims, 2 Drawing Sheets

SEQUENCE LISTING

```
<160> NUMBER OF SEQ ID NOS: 12

<210> SEQ ID NO 1
<211> LENGTH: 78
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is D or N
<220> FEATURE:
<221> NAME/KEY: MISC_FEATURE
<222> LOCATION: (9)..(10)
<223> OTHER INFORMATION: Xaa is D or N
<220> FEATURE:
<221> NAME/KEY: MISC_FEATURE
<222> LOCATION: (11)..(11)
<223> OTHER INFORMATION: Xaa is L or K
<220> FEATURE:
<221> NAME/KEY: MISC_FEATURE
<222> LOCATION: (12)..(12)
<223> OTHER INFORMATION: Xaa is E or T
<220> FEATURE:
<221> NAME/KEY: MISC_FEATURE
<222> LOCATION: (15)..(15)
<223> OTHER INFORMATION: Xaa is E or K
<220> FEATURE:
<221> NAME/KEY: MISC_FEATURE
<222> LOCATION: (20)..(20)
<223> OTHER INFORMATION: Xaa is E or T
<220> FEATURE:
<221> NAME/KEY: MISC_FEATURE
<222> LOCATION: (22)..(22)
<223> OTHER INFORMATION: Xaa is I or Q
<220> FEATURE:
<221> NAME/KEY: MISC_FEATURE
<222> LOCATION: (23)..(23)
<223> OTHER INFORMATION: Xaa is R or K
<220> FEATURE:
<221> NAME/KEY: MISC_FEATURE
<222> LOCATION: (26)..(26)
<223> OTHER INFORMATION: Xaa is R or K
<220> FEATURE:
```

```
<221> NAME/KEY: MISC_FEATURE
<222> LOCATION: (28)..(28)
<223> OTHER INFORMATION: Xaa is F or H
<220> FEATURE:
<221> NAME/KEY: MISC_FEATURE
<222> LOCATION: (29)..(29)
<223> OTHER INFORMATION: Xaa is A or N
<220> FEATURE:
<221> NAME/KEY: MISC_FEATURE
<222> LOCATION: (37)..(37)
<223> OTHER INFORMATION: Xaa is D or N
<220> FEATURE:
<221> NAME/KEY: MISC_FEATURE
<222> LOCATION: (40)..(40)
<223> OTHER INFORMATION: Xaa is D or S
<220> FEATURE:
<221> NAME/KEY: MISC_FEATURE
<222> LOCATION: (42)..(42)
<223> OTHER INFORMATION: Xaa is E or Q
<220> FEATURE:
<221> NAME/KEY: MISC_FEATURE
<222> LOCATION: (44)..(44)
<223> OTHER INFORMATION: Xaa is R or T
<220> FEATURE:
<221> NAME/KEY: MISC_FEATURE
<222> LOCATION: (49)..(49)
<223> OTHER INFORMATION: Xaa is P or S
<220> FEATURE:
<221> NAME/KEY: MISC_FEATURE
<222> LOCATION: (50)..(50)
<223> OTHER INFORMATION: Xaa is E or T
<220> FEATURE:
<221> NAME/KEY: MISC_FEATURE
<222> LOCATION: (51)..(51)
<223> OTHER INFORMATION: Xaa is Q or T
<220> FEATURE:
<221> NAME/KEY: MISC_FEATURE
<222> LOCATION: (54)..(54)
<223> OTHER INFORMATION: Xaa is Q or K
<220> FEATURE:
<221> NAME/KEY: MISC_FEATURE
<222> LOCATION: (55)..(55)
<223> OTHER INFORMATION: Xaa is E or N
<220> FEATURE:
<221> NAME/KEY: MISC_FEATURE
<222> LOCATION: (59)..(59)
<223> OTHER INFORMATION: Xaa is E or Q
<220> FEATURE:
<221> NAME/KEY: MISC_FEATURE
<222> LOCATION: (61)..(61)
<223> OTHER INFORMATION: Xaa is E or Q
<220> FEATURE:
<221> NAME/KEY: MISC_FEATURE
<222> LOCATION: (62)..(62)
<223> OTHER INFORMATION: Xaa is R or K
<220> FEATURE:
<221> NAME/KEY: MISC_FEATURE
<222> LOCATION: (66)..(66)
<223> OTHER INFORMATION: Xaa is E or N

<400> SEQUENCE: 1

Glu Met Xaa Ile Arg Phe Arg Gly Xaa Xaa Xaa Xaa Ala Phe Xaa Lys
1               5                   10                  15

Ala Leu Lys Xaa Met Xaa Xaa Gln Ala Xaa Lys Xaa Xaa Gly Thr Val
            20                  25                  30

Thr Tyr Thr Leu Xaa Gly Asn Xaa Leu Xaa Ile Xaa Ile Thr Gly Val
        35                  40                  45

Xaa Xaa Xaa Val Arg Xaa Xaa Leu Ala Lys Xaa Ala Xaa Xaa Leu Ala
    50                  55                  60

Lys Xaa Phe Asn Ile Thr Val Thr Tyr Thr Ile Arg Gly Ser
65                  70                  75

<210> SEQ ID NO 2
```

```
<211> LENGTH: 78
<212> TYPE: PRT
<213> ORGANISM: Artificial Sequence
<220> FEATURE:
<223> OTHER INFORMATION: Synthetic

<400> SEQUENCE: 2

Glu Met Asp Ile Arg Phe Arg Gly Asp Asp Leu Glu Ala Phe Glu Lys
1               5                   10                  15

Ala Leu Lys Glu Met Ile Arg Gln Ala Arg Lys Phe Ala Gly Thr Val
            20                  25                  30

Thr Tyr Thr Leu Asp Gly Asn Asp Leu Glu Ile Arg Ile Thr Gly Val
        35                  40                  45

Pro Glu Gln Val Arg Lys Glu Leu Ala Lys Glu Ala Glu Arg Leu Ala
    50                  55                  60

Lys Glu Phe Asn Ile Thr Val Thr Tyr Thr Ile Arg Gly Ser
65                  70                  75

<210> SEQ ID NO 3
<211> LENGTH: 80
<212> TYPE: PRT
<213> ORGANISM: Artificial Sequence
<220> FEATURE:
<223> OTHER INFORMATION: Synthetic

<400> SEQUENCE: 3

Glu Met Asn Ile Arg Phe Arg Gly Asn Asn Lys Thr Ala Phe Lys Lys
1               5                   10                  15

Ala Leu Lys Thr Met Gln Lys Gln Ala Lys Lys His Asn Gly Thr Val
            20                  25                  30

Thr Tyr Thr Leu Asn Gly Asn Ser Leu Gln Ile Thr Ile Thr Gly Val
        35                  40                  45

Ser Thr Thr Val Arg Gln Asn Leu Ala Lys Gln Ala Gln Lys Leu Ala
    50                  55                  60

Lys Asn Phe Asn Ile Thr Val Thr Tyr Thr Ile Arg Gly Ser Trp Ser
65                  70                  75                  80

<210> SEQ ID NO 4
<211> LENGTH: 74
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (69)..(74)
<223> OTHER INFORMATION: optionally absent

<400> SEQUENCE: 4

Met Asp Tyr Lys Asp Asp Asp Lys Gly Ser His Met Ala Ser Thr
1               5                   10                  15

Arg Gly Ser Gly Arg Pro Trp Lys Phe Ser Glu Asn Ile Ala Phe Glu
            20                  25                  30

Ile Ala Leu Ser Phe Thr Asn Lys Asp Thr Pro Asp Arg Trp Lys Lys
        35                  40                  45

Val Ala Gln Tyr Val Lys Gly Arg Thr Pro Glu Val Lys Lys His
    50                  55                  60

Tyr Glu Leu Glu His His His His His His
65                  70

<210> SEQ ID NO 5
```

```
<211> LENGTH: 74
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (69)..(74)
<223> OTHER INFORMATION: optionally absent

<400> SEQUENCE: 5

Met Asp Tyr Lys Asp Asp Asp Lys Gly Ser His Met Ala Ser Thr
1               5                   10                  15

Arg Gly Ser Gly Arg Pro Trp Lys Phe Ser Glu Asn Ile Ala Phe Glu
            20                  25                  30

Ile Ala Leu Ser Phe Thr Asn Lys Asp Thr Pro Asp Arg Trp Lys Lys
        35                  40                  45

Val Ala Gln Tyr Val Lys Gly Arg Thr Pro Glu Glu Val Lys Cys His
    50                  55                  60

Tyr Glu Leu Glu His His His His His
65                  70

<210> SEQ ID NO 6
<211> LENGTH: 95
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (90)..(95)
<223> OTHER INFORMATION: optionally absent

<400> SEQUENCE: 6

Met Asp Tyr Lys Asp Asp Asp Lys Gly Ser His Met Ala Ser Thr
1               5                   10                  15

Arg Gly Ser Gly Arg Pro Trp Lys Phe Ser Glu Asn Ile Ala Phe Glu
            20                  25                  30

Ile Ala Leu Ser Phe Thr Asn Lys Asp Thr Pro Asp Arg Trp Lys Lys
        35                  40                  45

Val Ala Gln Tyr Val Lys Gly Arg Thr Pro Glu Glu Val Lys Lys His
    50                  55                  60

Tyr Glu Leu Glu Gly Ser Leu Glu Gly Leu Asn Asp Ile Phe Glu Ala
65                  70                  75                  80

Gln Lys Ile Glu Trp His Glu Gly Ser His His His His His
                85                  90                  95

<210> SEQ ID NO 7
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (109)..(114)
<223> OTHER INFORMATION: optionally absent

<400> SEQUENCE: 7

Met Gly Asp Tyr Lys Asp Asp Asp Lys Gly Ser His Met Ser Asn
1               5                   10                  15

Ala Met Asp Gly Gln Gln Leu Asn Arg Leu Leu Leu Glu Trp Ile Gly
            20                  25                  30
```

Ala Trp Asp Pro Phe Gly Leu Gly Lys Asp Ala Tyr Asp Tyr Glu Ala
            35                  40                  45

Ala Glu Val Leu Lys Ala Val Tyr Glu Thr Glu Ser Ala Phe Asp Leu
 50                  55                  60

Ala Met Arg Ile His Trp Ile Tyr Asn Phe Ala Phe Lys Arg Gln Ile
 65                  70                  75                  80

Pro Phe Ala His Ala Gln Lys Leu Ala Arg Arg Leu Leu Glu Leu Lys
                 85                  90                  95

Gln Ala Ala Ser Ser Pro Leu Pro Leu Glu Gly Ser His His His His
             100                 105                 110

His His

<210> SEQ ID NO 8
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (109)..(114)
<223> OTHER INFORMATION: optionally absent

<400> SEQUENCE: 8

Met Gly Asp Tyr Lys Asp Asp Asp Lys Gly Ser His Met Ser Asn
 1               5                  10                  15

Ala Met Asp Gly Gln Gln Leu Asn Arg Leu Leu Leu Glu Trp Ile Gly
             20                  25                  30

Cys Trp Asp Pro Phe Gly Leu Gly Lys Asp Ala Tyr Asp Tyr Glu Ala
            35                  40                  45

Ala Glu Val Leu Lys Ala Val Tyr Glu Thr Glu Ser Ala Phe Asp Leu
 50                  55                  60

Ala Met Arg Ile His Trp Ile Tyr Asn Phe Ala Phe Lys Arg Gln Ile
 65                  70                  75                  80

Pro Phe Ala His Ala Gln Lys Leu Ala Arg Arg Leu Leu Glu Leu Lys
                 85                  90                  95

Gln Ala Ala Ser Ser Pro Leu Pro Leu Glu Gly Ser His His His His
             100                 105                 110

His His

<210> SEQ ID NO 9
<211> LENGTH: 132
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (127)..(132)
<223> OTHER INFORMATION: optionally absent

<400> SEQUENCE: 9

Met Asp Tyr Lys Asp Asp Asp Lys Gly Ser His Met Ser Asn Ala
 1               5                  10                  15

Met Asp Gly Gln Gln Leu Asn Arg Leu Leu Leu Glu Trp Ile Gly Ala
             20                  25                  30

Trp Asp Pro Phe Gly Leu Gly Lys Asp Ala Tyr Asp Tyr Glu Ala Ala
            35                  40                  45

Glu Val Leu Lys Ala Val Tyr Glu Thr Glu Ser Ala Phe Asp Leu Ala
 50                  55                  60

Met Arg Ile His Trp Ile Tyr Asn Phe Ala Phe Lys Arg Gln Ile Pro
65                  70                  75                  80

Phe Ala His Ala Gln Lys Leu Ala Arg Arg Leu Leu Glu Leu Lys Gln
                85                  90                  95

Ala Ala Ser Ser Pro Leu Pro Leu Glu Gly Ser Leu Gly Leu Asn
            100                 105                 110

Asp Ile Phe Glu Ala Gln Lys Ile Glu Trp His Glu Gly Ser His His
        115                 120                 125

His His His His
        130

<210> SEQ ID NO 10
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: optionally absent
<220> FEATURE:
<221> NAME/KEY: MISC_FEATURE
<222> LOCATION: (86)..(90)
<223> OTHER INFORMATION: optionally absent

<400> SEQUENCE: 10

Ser Asn Ala Met Asp Gly Gln Gln Leu Asn Arg Leu Leu Leu Glu Asn
1               5                   10                  15

Ile Gly Ala Trp Asp Pro Phe Gly Leu Gly Lys Asp Ala Tyr Thr Tyr
            20                  25                  30

Gln Ala Ala Glu Val Leu Lys Ala Val Tyr Glu Thr Asn Arg Ala Phe
        35                  40                  45

Asp Leu Ala Met Arg Ile His Trp Ile Tyr Asn Phe Ala Phe Lys Arg
    50                  55                  60

Arg Ile Pro Phe Ala Arg Thr Gln Lys Leu Ala Arg Arg Leu Leu Glu
65                  70                  75                  80

Leu Lys Gln Ala Ala Ser Ser Pro Leu Pro
                85                  90

<210> SEQ ID NO 11
<211> LENGTH: 240
<212> TYPE: DNA
<213> ORGANISM: Artificial Sequence
<220> FEATURE:
<223> OTHER INFORMATION: Synthetic

<400> SEQUENCE: 11
gaaatggata ttcgctttcg tggcgatgat ctggaagcgt ttgaaaaagc cctgaaagaa      60
atgattcgtc aggcgcgtaa atttgcgggc accgtgacct ataccctgga tggcaatgat    120
ctggaaattc gtattaccgg cgtgccgaaa caggtgcgta agaactggc gaaagaagcg     180 gaacgcctgg cgaaagaatt taacattacc gttacctata ccattcgcgg cagcctcgag    240

<210> SEQ ID NO 12
<211> LENGTH: 246
<212> TYPE: DNA
<213> ORGANISM: Artificial Sequence
<220> FEATURE:
<223> OTHER INFORMATION: Synthetic

<400> SEQUENCE: 12

```
gaaatgaaca ttcgttttcg cggcaacaat aaaaccgcat tcaagaaagc gctgaaaacc          60
atgcagaaac aagcgaaaaa acataatggc accgtcacgt ataccctgaa cggtaatagt         120
ctgcagatta cgatcaccgg cgtgagcacc acggttcgtc aaaacctggc gaaacaggcc         180
caaaaactgg caaaaaactt caacatcacg gttacctaca cgatccgcgg tagctggtct         240
ctcgag                                                                    246
```

POROUS MEMBRANE-BINDING PEPTIDES

CROSS REFERENCE

This application claims priority to U.S. Provisional Patent Application Ser. No. 62/222,118 filed Sep. 22, 2015, incorporated by reference herein in its entirety.

STATEMENT REGARDING FEDERALLY SPONSORED RESEARCH

This invention was made with U.S. government support under 5R01AI096184-05 and 2 R01 GM 092802-06, awarded by the National Institutes of Health. The U.S. Government has certain rights in the invention.

BACKGROUND

Lateral flow assays rely on strong adsorption between the capture element, whether a protein or antibody, and the target of interest. It is preferable that capture elements adsorb rapidly and robustly to a porous matrix for application in diagnostic development. Without rapid and robust adsorption between the capture element and the porous matrix capture elements move under capillary flow making detection more difficult.

SUMMARY OF THE INVENTION

In a first aspect, the invention provides polypeptides comprising the amino acid sequence of SEQ ID NO:1. In various embodiments, the polypeptide may comprise the amino acid sequence selected from the group consisting of SEQ ID NOS: 2-3. In a further embodiment, the invention provides fusion proteins, comprising one or more polypeptide of the invention and a second polypeptide. In one embodiment, the second polypeptide binds to an analyte of interest, including but not limited to a hemagglutinin protein. In various non-limiting embodiments, the second polypeptide comprises a polypeptide having the amino acid sequence selected from the group consisting of SEQ ID NO:4, SEQ ID NO:5, SEQ ID NO:6, SEQ ID NO:6, SEQ ID NO:7, SEQ ID NO:8, SEQ ID NO:9, and SEQ ID NO:10. In one embodiment, the polypeptide and the second polypeptide may be linked through an amino acid linker.

In another embodiment, the polypeptides or fusion proteins of the invention may further comprise a linked tag, including but not limited to a detectable moiety, a diagnostic agent, or a therapeutic agent. In another embodiment, the polypeptides or fusion proteins of the invention may be impregnated in or immobilized to a porous solid support, including but not limited to nitrocellulose.

In another aspect, the invention provides isolated nucleic acids encoding a polypeptide or fusion protein of the invention. In a further embodiment, the invention provides recombinant expression vectors comprising the nucleic acids or the invention operatively linked to a suitable control sequence. In a further embodiment, the invention provides host cells comprising a recombinant expression vector of the invention.

In another aspect, the invention provides methods for diagnosing an influenza infection, or monitoring progression of an influenza infection, comprising contacting a biological sample from a subject suspected of having an influenza infection with a diagnostically effective amount of one or more fusion polypeptides of the invention where the second polypeptide comprises and HA-binding polypeptide, under conditions suitable for binding of the polypeptide to a viral HA protein present in the sample; removing unbound polypeptide and/or sample; and detecting polypeptide-viral HA binding complexes, where the presence of such binding complexes indicates that the subject has an influenza infection, or provides a measure progression of an influenza infection.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1. Lateral flow challenge data for D1 protein and its derivatives, each run with an n=3. The three controls used were red food coloring to demonstrate the wet out area, monoclonal antibody to serve as an adsorption speed indicator, and the original D1 protein to serve as a direct comparison. All images on the left hand side of the pair were stained as is, and the images on the right were challenged with 5 mL of PBST before staining. The dotted line depicts the wet out area as determined by the red food coloring.

FIG. 2. Screening of the 3-helix and DI nitrocellulose-binding anchor proteins, with comparison to IgG. (A) Protein spots on nitrocellulose (GE FF80HP), subjected to lateral flow (LF) challenge with PBS or PBST or no LF control, and stained with Ponceau S. (B) Spot size relative to the full wet-out area indicated by the red food coloring (RFC), plotted as the mean+/−SD for n=4 replicates of each protein and n=6 replicates of the RFC control. Asterisk indicates that the 3-helix protein exhibits the smallest spot size ($p<0.025$). (C) Normalized pixel intensities of the Ponceau S-stained protein spots after LF challenge, plotted as the mean+/−SD.

DETAILED DESCRIPTION

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect the present application provides polypeptide comprising the amino acid sequence of SEQ ID NO:1:

| SEQ ID NO: 1 | |
| --- | --- |
| Residue number | Amino acids |
| 1 | E |
| 2 | M |
| 3 | D, N |
| 4 | I |
| 5 | R |
| 6 | F |
| 7 | R |
| 8 | G |
| 9 | D, N |
| 10 | D, N |
| 11 | L, K |
| 12 | E, T |
| 13 | A |
| 14 | F |
| 15 | E, K |
| 16 | K |
| 17 | A |
| 18 | L |
| 19 | K |
| 20 | E, T |
| 21 | M |
| 22 | I, Q |
| 23 | R, K |
| 24 | Q |
| 25 | A |
| 26 | R, K |
| 27 | K |
| 28 | F, H |
| 29 | A, N |
| 30 | G |
| 31 | T |
| 32 | V |
| 33 | T |
| 34 | Y |
| 35 | T |
| 36 | L |
| 37 | D, N |
| 38 | G |
| 39 | N |
| 40 | D, S |
| 41 | L |
| 42 | E, Q |
| 43 | I |
| 44 | R, T |
| 45 | I |
| 46 | T |
| 47 | G |
| 48 | V |
| 49 | P, S |
| 50 | E, T |
| 51 | Q, T |
| 52 | V |
| 53 | R |
| 54 | K, Q |
| 55 | E, N |
| 56 | L |

| SEQ ID NO: 1 | |
| --- | --- |
| Residue number | Amino acids |
| 57 | A |
| 58 | K |
| 59 | E, Q |
| 60 | A |
| 61 | E, Q |
| 62 | R, K |
| 63 | L |
| 64 | A |
| 65 | K |
| 66 | E, N |
| 67 | F |
| 68 | N |
| 69 | I |
| 70 | T |
| 71 | V |
| 72 | T |
| 73 | Y |
| 74 | T |
| 75 | I |
| 76 | R |
| 77 | G |
| 78 | S |

The polypeptides of the invention are capable of adsorbing strongly and specifically to a porous membrane. In certain embodiments, the polypeptides of the present application comprise portions that are highly positively charged by introducing large amount of arginine and lysine on protein surface. Additionally, the polypeptides are highly stable under ambient conditions. Both of these characteristics are beneficial for diagnostic development, as the positive charge facilitates adsorption with the negative charges commonly associated with porous matrices used in lateral flow assays and other diagnostic devices, such as nitrocellulose, and the stability enables the development of a device with more optimal shelf life.

In certain embodiments the polypeptides of the present application consist or comprise the following sequences:

```
D1 (2k18)
                                        (SEQ ID NO: 2)
EMDIRFRGDDLEAFEKALKEMIRQARKFAGTVTYTLDGNDLEIRITGVPE

QVRKELAKEAERLAKEFNITVTYTIRGS

2k18_superpos
                                        (SEQ ID NO: 3)
EMNIRFRGNNKTAFKKALKTMQKQAKKHNGTVTYTLNGNSLQITITGVST

TVRQNLAKQAQKLAKNFNITVTYTIRGSWS
```

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in de-immunized variants. Such linkage can be covalent or non-covalent as is understood by those of skill in the art.

In certain embodiments, the polypeptides of the present application are fusion peptides comprising a polypeptide of the invention and a second polypeptide. The second polypeptide can be any polypeptide of interest. In one embodiment, the second polypeptide binds to an analyte of interest, such that the fusion protein can be bound to a negatively charged porous membrane through the polypeptide of the invention, leaving the second free to bind to its analyte in a sample of interest. In this embodiment, the analyte of interest is a hemagglutinin protein. and the second polypeptide comprises or consists of a hemagglutinin-binding polypeptide. Such hemagglutinin-binding polypeptides are described, for example, in PCT application numbers PCT/US2015/021780, PCT/US2011/046414, PCT/US2013/030311, PCT/US2015/046920, and PCT/US2014/028358, each of which is incorporated herein in their entirety by reference.

In specific embodiments, the second polypeptide comprises one or more of the following polypeptides (residues in parentheses are optional):

```
HB80.4
                                        (SEQ ID NO: 4)
MDYKDDDDKGSHMASTRGSGRPWKFSENIAFEIALSFTNKDTPDRWKKVA

QYVKGRTPEEVKKHYELE(HHHHHH)

Cys-HB80.4
                                        (SEQ ID NO: 5)
MDYKDDDDKGSHMASTRGSGRPWKFSENIAFEIALSFTNKDTPDRWKKVA

QYVKGRTPEEVKCHYELE(HHHHHH)

AVI-HB80.4
                                        (SEQ ID NO: 6)
MDYKDDDDKGSHMASTRGSGRPWKFSENIAFEIALSFTNKDTPDRWKKVA

QYVKGRTPEEVKKHYELEGSLEGLNDIFEAQKIEWHEGS(HHHHHH)

HB36.5
                                        (SEQ ID NO: 7)
MGDYKDDDDKGSHMSNAMDGQQLNRLLLEWIGAWDPFGLGKDAYDYEAAE

VLKAVYETESAFDLAMRIHWIYNFAFKRQIPFAHAQKLARRLLELKQAAS

SPLPLEGS(HHHHHH)

Cys-11B36.5
                                        (SEQ ID NO: 8)
MGDYKDDDDKGSHMSNAMDGQQLNRLLLEWIGCWDPFGLGKDAYDYEAAE

VLKAVYETESAFDLAMRIHWIYNFAFKRQIPFAHAQKLARRLLELKQAAS

SPLPLEGS(HHHHHH)

AVI-HB36.5
                                        (SEQ ID NO: 9)
MDYKDDDDKGSHMSNAMDGQQLNRLLLEWIGAWDPFGLGKDAYDYEAAEV

LKAVYETESAFDLAMRIHWIYNFAFKRQIPFAHAQKLARRLLELKQAASS

PLPLEGSLEGLNDIFEAQKIEWHEGS(HHHHHH)

HB36.6
                                       (SEQ ID NO: 10)
(SNAMD)GQQLNRLLLEnIGAWDPFGLGKDAYtYqAAEVLKAVYETnrAF

DLAMRIHWIYNFAFKRrIPFArtQKlARRLLELKQAA(SSPLP)
```

In certain embodiments, the polypeptide of the invention and the second polypeptide are coupled through an amino acid linker. Any suitable amino acid linker can be used In certain embodiments the linker comprises a peptide sequence of between 1-100 amino acid residues.

In a further embodiment, the polypeptides of any embodiment of any aspect of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used diagnostically to, for example, assess if a subject has been infected with influenza virus or monitor the development or progression of an influenza virus infection as part of a clinical testing procedure to, e.g., determine the efficacy of a given treatment regimen. However, they may also be used for other detection and/or analytical and/or diagnostic purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis/diagnosis techniques and/or methods used such as immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples preferred tags are enzymes that catalyze production and local deposition of a detectable product. Enzymes typically conjugated to polypeptides to permit their immunohistochemical visualization are well known and include, but are not limited to, acetylcholinesterase, alkaline phosphatase, beta-galactosidase, glucose oxidase, horseradish peroxidase, and urease. Typical substrates for production and deposition of visually detectable products are also well known to the skilled person in the art. The polypeptides can be labeled using colloidal gold or they can be labeled with radioisotopes, such as 33P, 32P, 35S, 3H, and 125I. Polypeptides of the invention can be attached to radionuclides directly or indirectly via a chelating agent by methods well known in the art.

The polypeptides and fusion proteins of the invention can also be attached to porous solid supports, which are particularly useful for in vitro assays or purification of analytes (particularly when using the fusion proteins of the invention), for example, influenza virus or HA protein. Such porous solid supports might be planar or nonplanar and include, but are not limited to, glass, cellulose, nitrocellulose, polyacrylamide, nylon, polystyrene, polyvinyl chloride or polypropylene supports.

In certain embodiments, the present application provides a porous membrane comprising one or more the peptides impregnated or immobilized to a portion of the porous membrane. As used herein, a "porous membrane" refers to a porous membrane (e.g., a wick, pathway, leg, pad, delivery channel, etc.) through which fluid can travel by capillary action, such as paper, nitrocellulose, nylon, glass fiber, and the like. Unless the context clearly requires otherwise, a porous membrane can be two-dimensional or three-dimensional (when considering its height in addition to its length and width). Additionally, a porous membrane can be a single layer or may comprise two or more membranous layers.

Although in some embodiments a specific term may be used (e.g., "wick," "pathway," "leg," "pad," "delivery channel," etc.), it should be understood that use of a different porous membrane is also within the scope of the present technology.

In another aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In certain embodiments, the nucleic acid sequences of the present application comprise or consist of the following:

```
                                              (SEQ ID NO: 11)
GAAATGGATATTCGCTTTCGTGGCGATGATCTGGAAGCGTTTGAAAAAGC

CCTGAAAGAAATGATTCGTCAGGCGCGTAAATTTGCGGGCACCGTGACCT

ATACCCTGGATGGCAATGATCTGGAAATTCGTATTACCGGCGTGCCGGAA

CAGGTGCGTAAAGAACTGGCGAAAGAAGCGGAACGCCTGGCGAAAGAATT

TAACATTACCGTTACCTATACCATTCGCGGCAGCCTCGAG (SEQ ID NO: 12)
GAAATGAACATTCGTTTTCGCGGCAACAATAAAACCGCATTCAAGAAAGC

GCTGAAAACCATGCAGAAACAAGCGAAAAAACATAATGGCACCGTCACGT

ATACCCTGAACGGTAATAGTCTGCAGATTACGATCACCGGCGTGAGCACC

ACGGTTCGTCAAAACCTGGCGAAACAGGCCCAAAAACTGGCAAAAAACTT

CAACATCACGGTTACCTACACGATCCGCGGTAGCTGGTCTCTCGAG
```

In a further aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells comprising the recombinant expression vectors disclosed herein, wherein the host cells can be either prokaryotic or eukaryotic. The cells can be transiently or stably transfected, or the vector may be otherwise introduced into the host cells (electroporation, gene gun, etc.). Transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2nd Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In another aspect, the present invention provides methods for diagnosing an influenza infection, or monitoring progression of an influenza infection, comprising contacting a biological sample from a subject suspected of having an influenza infection with a diagnostically effective amount of one or more fusion polypeptides of the invention comprising a hemagglutinin binding domain under conditions suitable for binding of the polypeptide to a viral HA protein present in the sample; removing unbound polypeptide and/or sample; and detecting polypeptide-viral HA binding complexes, where the presence of such binding complexes indicates that the subject has an influenza infection, or provides a measure progression of an influenza infection. In certain embodiments, the fusion polypeptides of the present application are adsorbed to a porous matrix. In certain embodiments, the porous matrix is nitrocellulose. In various embodiments, the fusion protein comprises the polypeptide of SEQ ID NO:1, 2, or 3 expressed as a fusion with the second polypeptide being an HA-binding polypeptide. In various further embodiments, the second polypeptide in the fusion protein comprises the amino acid sequence of any one or more of SEQ ID NOS 4-10.

The methods of this aspect of the invention can be used to more accurately identify patients that may be suffering from an influenza infection and to thus provide more informed determination of treatment options by an attending caregiver. Individuals at risk of an influenza infection are as described above. The methods can also be used to monitor progression of an influenza infection; in this embodiment, the subject is known to be infected, and the methods can be used, for example, as a data point for an attending caregiver to determine whether to initiate, modify, or continue a particular course of therapy, such as treatment with neuraminidase or M2 protein inhibitors.

The biological sample may be any suitable biological sample including, but not limited to blood, serum, nasal secretions, tissue or other biological material from a subject at risk of infection.

EXAMPLES

Recombinant Flu Binder Preparation

In this work, three different versions of the previously developed flu HA binder (Hemagglutinin Binder) were used as base proteins: HB80.4 (8.7 kDa), HB36.5 (13.0 kDa), and HB36.6 (13.3 kDa). The HB80.x and HB36.x proteins are based on different scaffolds, but bind to the same stem region epitope of influenza HA. HB36.6 represents an iteration of HB36.5 that was further improved for stability and biding affinity. The amino acid sequences for HB36.6, HB80.4 and HB36.5, and the modifications developed herein, are disclosed as SEQ ID NOS: 4-10.

The recombinant influenza HA binders and nitrocellulose-binding anchor proteins were cloned, expressed in *E. coli*, and purified via metal affinity chromatography using Ni-NTA resin to recognize C-terminal His tags, as described previously. All flu HA binders contained N-terminal FLAG™ tags to aid visualization of the proteins when needed.

Membrane Preparation

Nitrocellulose membranes were cut into test strips or multi-legged devices using a $CO_2$ laser cutter (Universal Laser Systems, Scottsdale, Ariz.). In most cases, each test strip was 3 mm wide by 24 mm tall. Generally sets of 4 strips were cut together and connected by a 6-mm tall section at the top of the device in order to promote batch processing. The distance between strips was 6 mm, designed to allow each set of strips to fit into the wells of a 96-well plate.

Recombinant flu binder proteins were prepared as described above. Unless otherwise noted, all proteins were deposited onto the membrane strips using a piezoelectric printer (sciFLEXARRAYER™ S3, Scienion AG, Berlin, Germany). Proteins were prepared at 100 µM in HBS (10 mM HEPES, 150 mM NaCl, pH 7.4) or PBS (10 mM sodium phosphate, 138 mM NaCl, 2.7 mM KCl, pH 7.4), unless otherwise noted. To avoid clogging the printer plumbing with particulate from the samples, all protein solutions were filtered through a centrifugal filter device with 0.2-µm nylon membrane (VWR, Radnor, Pa.) at 6000 g for 5 minutes prior to spotting. Test lines were created by 12 spots spaced 250 µm apart, with 30 droplets per spot, and two passes were printed for each test line to saturate the membrane region. Each droplet was 450-500 pL, resulting in test lines comprising ~300 nL of protein solution in total. For the nitrocellulose-binding protein screening, circular spots were deposited using 1000 droplets at 450-500 pL per droplet, for ~500 nL in total. After spotting, membranes were stored under desiccation at least overnight, and up to one week, before use.

Immobilization Efficiency Testing: Lateral Flow Challenge

To screen the efficiency of each immobilization method, we used a lateral flow challenge system to evaluate how strongly a protein was immobilized to the membrane and to what extent it was subject to stripping by a challenge solution [16]. For the lateral flow challenge, strips were placed into a well (96-well plate for 3-mm-wide strips, multi-channel pipette reservoir for 0.8-cm-wide strips) filled with the given challenge solution (50 µL and 5 mL, respectively). A cellulose absorbent pad (Millipore #CFSP223000) cut to the width of the device and 70 mm tall was secured to the top of the nitrocellulose device to aid wicking, either with tape or with a custom-made plastic housing. The challenge solution was allowed to wick through the strips for 15 minutes, at which point the strips were removed from the solution. In this work, challenge solutions included deionized $H_2O$, phosphate-buffered saline (PBS, pH 7.4, Sigma-Aldrich, St. Louis, Mo.), and PBS+0.1% v/v Tween-20 (PBST).

Figure 1:
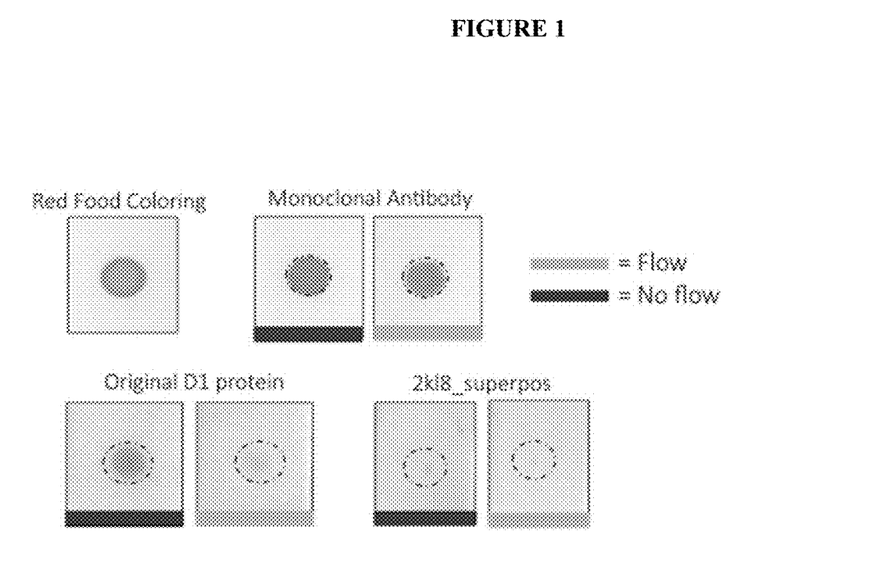

The amount of protein remaining on the membrane was visualized in one of three ways, as illustrated in FIG. 1A: staining with a specific FITC-labeled anti-FLAG™ tag antibody, nonspecific protein staining with Coomassie Brilliant Blue™ (Thermo Scientific #20278, Life Technologies, Carlsbad, Calif.), or nonspecific protein staining with Ponceau S™ (Thermo Scientific #24580). For Coomassie staining, each membrane was incubated for 10 minutes with stain solution, followed by 10 minutes with destain solution, both with shaking. This protocol, adapted from Metkar et al., uses a destain solution of 50% $H_2O$, 40% methanol, and 10% glacial acetic acid, and a stain solution of 0.0025% w/v Coomassie Brilliant Blue in destain solution. For Ponceau S staining, each membrane was incubated with shaking for 5 minutes with stain solution (0.1% w/v Ponceau S in 5% acetic acid), followed by 2 minutes with $H_2O$ for destaining, as based on the manufacturer's protocol and optimized in-house. In both cases, the stained devices were taped to a standard piece of printer paper and imaged at 48-bit HDR color, 600 dpi, $\gamma=1$ using a desktop scanner (Perfection V700 Photo Scanner, Epson, Long Beach, Calif.).

In the case of FITC-anti-FLAG™ tag staining, this fluorescently labeled antibody was used to specifically recognize the FLAG™ tag present in the recombinant HA binders. In these experiments, FITC-anti-FLAG™ (Sigma-Aldrich #F4049) was diluted to a working concentration of 100 µg/mL in fetal bovine serum (FBS, Gibco #16000-077, Life Technologies), which prevents the antibody from adsorbing nonspecifically to the membrane. This FITC-anti-FLAG™ solution was then applied to the strips via lateral flow, using 20 µL of solution per well of a 96-well plate, followed by a rinse with 40 µL buffer (PBS). The resulting fluorescently stained membranes were visualized by imaging under ultraviolet (UV) excitation using a commercial UV gel imager (Gel Doc EZ™ System, Bio-Rad, Hercules, Calif.). This imager utilizes a UV sample tray (Bio-Rad #170-8271) to achieve UV illumination of the membrane from broadband light, with the strength of fluorescence signal being controlled by the time of exposure. Membranes were imaged backing-side-up, as this orientation was determined to give the lowest background fluorescence.

Protein Functionality Testing: Flu HA Assay

Since protein immobilization efficiency only tells us how well the protein stays on the membrane, we also wanted to determine how functional the protein was for a given immobilization strategy. To test this functionality, each immobilization strategy was tested using the recombinant HA binder as a capture agent for an influenza HA assay. All assays utilized standard antibody-based detection to complete the assay sandwich, in order to focus solely on improvements gained by the immobilization method.

Nitrocellulose strips were prepared with test lines patterned with recombinant flu HA binder as described above. Each flu assay was performed in a dipstick lateral flow format using a 96-well plate pre-loaded with the given assay reagents, and the test strips were manually moved between wells to initiate each assay step. A cellulose absorbent pad (Millipore #CFSP223000) cut to the width of the device and 70 mm tall was secured to the top of the nitrocellulose device to aid wicking, either with tape or with a custom-made plastic housing. Unless otherwise noted, each assay consisted of the following steps: 1) 20 μL recombinant HA or negative control, 2) 20 μL wash, 3) 20 μL mouse anti-HA detection antibody, 4) 20 μL wash, 5) 20 μL gold-conjugated goat-anti-mouse IgG antibody, and 6) 20 μL wash. Recombinant HA was from one of three influenza strains, as indicated: A/New Caledonia/20/1999 (Protein Sciences, Meriden, Conn.), A/California/04/2009 (Influenza Reagent Resource (IRR)), or A/Solomon Islands/03/2006 (IRR), all of which are H1N1 strains. Matching detection antibodies were used accordingly. The gold-conjugated secondary (Au-2°) antibody (Au-goat-anti-mouse IgG, Arista Biologicals, Inc., Allentown, Pa.) was used at optical density (OD) 2.5. All reagents were diluted in a running buffer of PBS or PBST+1% w/v bovine serum albumin (BSA, Sigma-Aldrich #A7030). Wash buffer was either PBS or PBST, as indicated. The generic assay stack is illustrated in FIG. 1B. After the assay was complete, the wicking pads were removed, and all devices were taped to a standard piece of printer paper and imaged at 48-bit HDR color, 600 dpi, γ=1 using a desktop scanner (Epson Perfection™ V700 Photo Scanner).

Signal Quantification

All signal intensities from protein lines and test lines were quantified using a custom script in MATLAB™ (Math-Works, Natick, Mass.). Using this program, a region of interest (ROI) is drawn semi-manually around the test line of interest, and the average pixel intensity inside this test ROI, $I_{test}$, is computed. This value is then background-subtracted using the average pixel intensity inside a local background region, $I_{bkgd}$, and normalized on a scale from 0 to 1 to generate the normalized pixel intensity of the spot, $I_{norm}$, using Eqn 1.

$$I_{norm} = \frac{I_{test} - I_{bkgd}}{0 - I_{bkgd}} \quad \text{Eqn 1}$$

For each experiment, the channel of the RGB image that was most sensitive to the particular color of signal was chosen for analysis. For the flu HA assays (red color from gold nanoparticles) and the Ponceau S™-stained membranes (pink color), the green channel was used. For the Coomassie-stained membranes, the red channel was used. Finally, for the fluorescence images based on FITC-anti-FLAG signal, inverted grayscale quantification was used (signal=white, background=black). In all cases, the normalized pixel intensities represent a range from no signal (0) to maximum possible signal (1).

For the protein spots used in the nitrocellulose-binding anchor protein screening, the area of each protein spot was first determined. Specifically, another custom MATLAB™ script was used to conduct edge-finding of the spots based on the derivative of pixel intensity, and then fit the edges with ellipses using a least-squares fitting algorithm. The area of each resulting ellipse was then reported as the area of the given protein spot. The average pixel intensity inside this spot area was computed and used to determine the normalized pixel intensity as described by Eqn 1.

For significance testing between two sets of data, the Student's t-test was used. Unless otherwise specified, a one-tailed, unpaired t-test assuming unequal variance was applied, with a significance threshold of α=0.025. The one-tailed test was chosen to select for unidirectional differences in signal.

Nitrocellulose-Binding Anchor Protein Provides Close Mimic to Streptavidin-Biotin System at Lower Cost In order to develop a lower-cost alternative to the mutant streptavidin-biotin anchoring system, we sought to develop a fusion of the recombinant flu binder protein to a custom nitrocellulose-binding anchor protein. To do so, we first screened several computationally designed proteins for their ability to adsorb robustly to nitrocellulose in order to identify anchor protein candidates. We screened a set of five globular proteins engineered to have ideal energy landscapes and therefore high stability, in addition to a 3-helix bundle protein designed to be ultra-stable and have an ideal coating of positive charge, due to its high lysine content (25% lysine by amino acid). This lysine content confers to the protein a high isoelectric point (pI) of 9.4, which is ideal according to both protein adsorption theory and supporting experimental results. Of the proteins initially screened, both the Design I (DI) globular protein (SEQ ID NO:2) and the 3-helix bundle protein (SEQ ID NO:3) showed promising adsorption to nitrocellulose, so these were further characterized and compared to IgG, which is known to adsorb robustly. Key properties of the two nitrocellulose-binding anchor protein candidates are summarized in Table 1.

TABLE 1

Protein parameters for the two nitrocellulose-binding anchor candidates, 3-helix and DI

|  | 3-helix | DI |
| --- | --- | --- |
| PDB Identifier | 4TQL | 2KL8 |
| Molecular weight | 29.6 kDa | 10.1 kDa |
| Isoelectric point | 9.4 | 6.3 |
| Lysine content | 25% | 7% |

Figure 2:
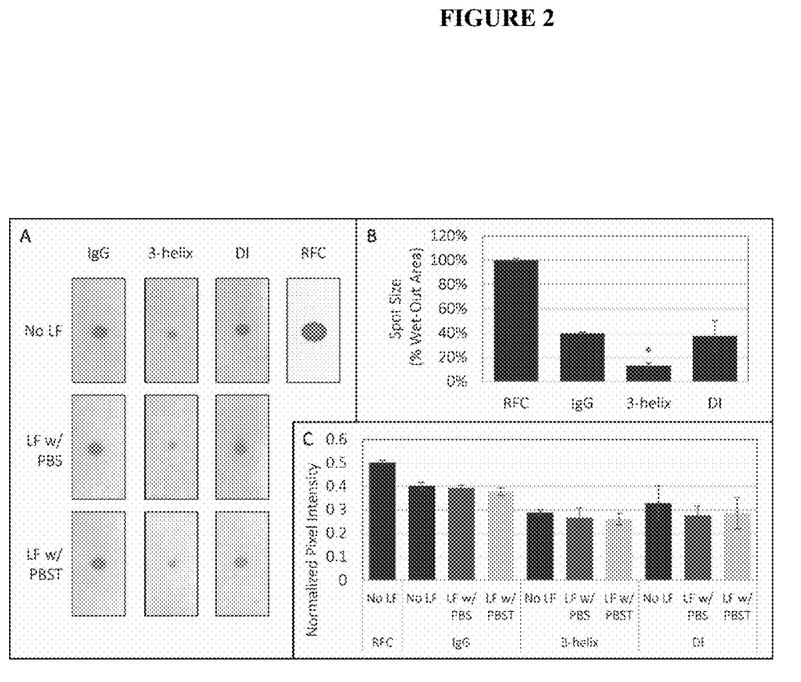

The adsorption of the DI protein, 3-helix protein, and IgG were compared using the lateral flow challenge method. In this case, 0.8-cm-wide strips were used (GE FF80HP nitrocellulose), and proteins were deposited at 1 mg/mL in PBS as spots using 1000 droplets at 450-500 pL per droplet. Red food coloring diluted 1:10 in $H_2O$ was also patterned at the same volume in order to visualize the full wet-out area of that volume. Challenge solutions of PBS and PBST were used, along with a no lateral flow control. The protein remaining at each test spot was visualized using Ponceau S staining, as described above. A representative test spot for each condition is shown in FIG. 2A. The area of each spot relative to the full wet-out area given by the red food coloring is plotted in FIG. 2B as the mean+/−SD for n=4 replicates of each protein spot and n=6 replicates for the red food coloring control. The normalized green-channel pixel intensity inside each spot is plotted in FIG. 2C as the mean+/−SD for n=4 replicates of each protein spot and n=6 replicates for the red food coloring control. The small sizes of the protein spots relative to the full wet-out area reveal that all three proteins adsorb to the membrane quickly, which is ideal for anchor protein candidates. In fact, the 3-helix protein yields the smallest spot size (p<0.025), indicating that it adsorbs to nitrocellulose the most rapidly.

The DI protein yields a spot size similar to IgG (no significant difference), signifying that it also adsorbs quickly to the membrane. All three proteins are also resistant to stripping under lateral flow challenge with PBS and PBST, with no significant difference in the spot intensity relative to the no LF control for the given protein (p>0.025).

Overall, these results indicate that all three proteins adsorb robustly to the nitrocellulose membrane and are strong candidates for nitrocellulose-binding anchor proteins. While this strong adsorption profile was expected for the 3-helix protein, due to its ideal isoelectric point, the strong adsorption of the DI protein was not expected based on its pI alone. We therefore hypothesize that the robust adsorption of the 3-helix and DI proteins is partially due to the favorable electrostatics of the systems, in addition to favorable hydrophobic properties that are less well understood. The theoretical design of anchor proteins like these therefore has much room for improvement and represents an opportune area for future investigation. Nevertheless, our current approach yielded two successful anchor protein candidates, one of which was strongly guided by adsorption theory.

Given the successful adsorption of the 3-helix and DI proteins, we prepared genetic fusions of the stem region flu binder (HB36.6) to each of these nitrocellulose anchor proteins. The 3-helix-binder fusion protein did not express well in our recombinant expression system, so further studies focused on the DI protein. The DI-binder fusion protein (DI-HB36.6) did express successfully and was tested for functionality as a capture agent for the flu HA assay on GE FF80HP nitrocellulose. The assay was run using recombinant HA from A/Solomon Islands/03/2006 influenza (Influenza Reagent Resource (IRR) #FR-67) at 10 nM and accompanying mouse-anti-HA antibody (IRR #FR-502) at 100 nM. All reagents were diluted in a running buffer of PBST+BSA, and PBST was used for all washes in this experiment. The results indicate that the DI-binder fusion serves as an effective capture agent for the flu HA assay, producing a strong signal for the test sample and a clean negative control.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

We claim:

1. A polypeptide comprising the amino acid sequence of SEQ ID NO:1.

2. The polypeptide of claim 1, comprising the amino acid sequence selected from the group consisting of SEQ ID NOS: 2-3.

3. A fusion protein, comprising (a) one or more polypeptide of claim 1, and (b) a second polypeptide.

4. The fusion protein of claim 3, wherein the second polypeptide binds to an analyte of interest.

5. The fusion protein of claim 4, wherein the analyte of interest is a hemagglutinin protein.

6. The fusion protein of claim 5, wherein the second polypeptide comprises a polypeptide having the amino acid sequence selected from the group consisting of SEQ ID NO:4, SEQ ID NO:5, SEQ ID NO:6, SEQ ID NO:6, SEQ ID NO:7, SEQ ID NO:8, SEQ ID NO:9, and SEQ ID NO:10.

7. The fusion protein of claim 3, wherein the polypeptide of claim 1 and the second polypeptide are coupled through an amino acid linker.

8. The polypeptide of claim 1, further comprising a tag linked to the polypeptide.

9. The polypeptide of claim 1, wherein the tag comprises a detectable moiety, a diagnostic agent, or a therapeutic agent.

10. The fusion protein of claim 3, further comprising a tag linked to the fusion protein.

11. The fusion protein of claim 10, wherein the tag comprises a detectable moiety, a diagnostic agent, or a therapeutic agent.

12. The polypeptide of claim 1 impregnated in or immobilized to a porous solid support.

13. The polypeptide of claim 12, wherein the porous solid support comprises nitrocellulose.

14. The fusion protein of claim 3 impregnated in or immobilized to a porous solid support.

15. The fusion protein of claim 14, wherein the porous solid support comprises nitrocellulose.

16. A nucleic acid encoding the polypeptide of claim 1.

17. A recombinant expression vector comprising the nucleic acid of claim 16 operatively linked to a suitable control sequence.

18. A host cell comprising the recombinant expression vector of claim 17.

19. A method for diagnosing an influenza infection, or monitoring progression of an influenza infection, comprising contacting a biological sample from a subject suspected of having an influenza infection with a diagnostically effective amount of one or more fusion polypeptides of claim 6, under conditions suitable for binding of the polypeptide to a viral HA protein present in the sample; removing unbound polypeptide and/or sample; and detecting polypeptide-viral HA binding complexes, where the presence of such binding complexes indicates that the subject has an influenza infection, or provides a measure of progression of an influenza infection.

* * * * *